(12) United States Patent
Arndt et al.

(10) Patent No.: US 8,878,679 B2
(45) Date of Patent: Nov. 4, 2014

(54) BABY MONITOR LIGHT

(71) Applicants: Alissa Arndt, Mentor, OH (US);
Michael Arndt, Mentor, OH (US)

(72) Inventors: Alissa Arndt, Mentor, OH (US);
Michael Arndt, Mentor, OH (US)

( * ) Notice: Subject to any disclaimer, the term of this patent is extended or adjusted under 35 U.S.C. 154(b) by 0 days.

(21) Appl. No.: 13/894,548

(22) Filed: May 15, 2013

(65) Prior Publication Data
US 2013/0308305 A1 Nov. 21, 2013

Related U.S. Application Data

(60) Provisional application No. 61/648,070, filed on May 16, 2012.

(51) Int. Cl.
| | | |
|---|---|---|
| G08B 1/08 | (2006.01) | |
| G08B 13/14 | (2006.01) | |
| F21V 15/00 | (2006.01) | |
| F21V 21/00 | (2006.01) | |
| F21V 21/08 | (2006.01) | |
| F21L 4/00 | (2006.01) | |
| F21L 13/00 | (2006.01) | |
| F21V 33/00 | (2006.01) | |
| A45C 15/06 | (2006.01) | |
| F21V 21/26 | (2006.01) | |
| F21V 7/00 | (2006.01) | |
| A61B 5/113 | (2006.01) | |
| F21L 4/08 | (2006.01) | |

(52) U.S. Cl.
CPC .............. *F21V 33/0004* (2013.01); *F21V 7/00* (2013.01); *A61B 5/113* (2013.01); *F21L 4/08* (2013.01); *A61B 2503/04* (2013.01)

USPC .............. 340/573.1; 340/539.15; 340/539.14; 340/572.1; 362/103; 362/154; 362/156; 362/253; 362/269; 362/365; 362/396; 362/183

(58) Field of Classification Search
USPC ......... 362/103, 154–156, 253, 269, 365, 396, 362/183; 340/539.15, 539.14, 572.1, 573.1
See application file for complete search history.

(56) References Cited

U.S. PATENT DOCUMENTS

| 3,926,177 A | 12/1975 | Hardway, Jr. et al. |
| 4,146,885 A * | 3/1979 | Lawson, Jr. .................... 600/534 |

(Continued)

FOREIGN PATENT DOCUMENTS

| JP | 05161613 A * | 6/1993 |
| WO | WO 2012164482 A1 * | 12/2012 |

OTHER PUBLICATIONS

Translation of JP 05161613 A, all 7 pages.*

(Continued)

*Primary Examiner* — Daniel Wu
*Assistant Examiner* — Emily C Terrell
(74) *Attorney, Agent, or Firm* — Hahn Loeser & Parks, LLP (57) ABSTRACT

A baby monitoring light system includes a light body having a bottom portion and a top portion, the light body having a height generally shorter than the light body width and length, the light body comprising a light source oriented upwardly from the top portion, the light body adapted to project a light beam upwardly onto a surface approximately 5 to 15 feet away. The system may include a blanket having a pocket, the light body positionable in the pocket, the pocket having a space through which the light source projects when the light body is in the pocket. The light body may include one or more releasable fasteners.

16 Claims, 10 Drawing Sheets

(56) References Cited

U.S. PATENT DOCUMENTS

| | | | |
|---|---|---|---|
| 4,148,313 A | 4/1979 | Bird et al. | |
| 4,366,821 A | 1/1983 | Wittmaier et al. | |
| 4,657,025 A | 4/1987 | Orlando | |
| 4,679,036 A * | 7/1987 | Cheng | 340/573.1 |
| 4,924,876 A | 5/1990 | Cameron | |
| 5,241,300 A * | 8/1993 | Buschmann | 340/573.1 |
| 5,400,012 A * | 3/1995 | Walton | 340/573.1 |
| 5,454,376 A | 10/1995 | Stephens et al. | |
| 5,684,460 A * | 11/1997 | Scanlon | 340/573.1 |
| 5,914,660 A * | 6/1999 | Mesibov et al. | 340/573.7 |
| 6,043,747 A | 3/2000 | Altenhofen | |
| 6,054,926 A | 4/2000 | Deleo | |
| 6,184,791 B1 * | 2/2001 | Baugh | 340/576 |
| 6,185,446 B1 | 2/2001 | Carlsen, Jr. | |
| 6,253,380 B1 * | 7/2001 | Larsson et al. | 2/114 |
| 6,280,392 B1 | 8/2001 | Yoshimi et al. | |
| 6,377,177 B1 * | 4/2002 | Broussard et al. | 340/573.1 |
| 6,765,489 B1 * | 7/2004 | Ketelhohn | 340/573.1 |
| 6,980,679 B2 | 12/2005 | Jeung et al. | |
| 7,035,432 B2 | 4/2006 | Szuba | |
| 7,049,968 B2 | 5/2006 | Fitzgerald et al. | |
| 7,123,758 B2 | 10/2006 | Jeung et al. | |
| 7,306,564 B2 | 12/2007 | Nakatani et al. | |
| 7,403,638 B2 | 7/2008 | Jeung et al. | |
| 7,431,700 B2 * | 10/2008 | Aoki et al. | 600/534 |
| 7,471,539 B2 | 12/2008 | Oates et al. | |
| 7,545,279 B2 * | 6/2009 | Sato et al. | 340/573.1 |
| 7,575,554 B2 | 8/2009 | Onishi | |
| 7,670,026 B1 * | 3/2010 | Hawkins | 362/249.05 |
| 7,678,063 B2 | 3/2010 | Felmlee et al. | |
| 7,697,891 B2 | 4/2010 | Desrosiers et al. | |
| 8,094,013 B1 * | 1/2012 | Lee et al. | 340/539.15 |
| 2002/0097155 A1 | 7/2002 | Cassel et al. | |
| 2002/0124295 A1 * | 9/2002 | Fenwick et al. | 2/69 |
| 2004/0005088 A1 | 1/2004 | Jeung et al. | |
| 2005/0102752 A1 * | 5/2005 | Abraham et al. | 5/482 |
| 2006/0103522 A1 | 5/2006 | Spencer | |
| 2008/0024311 A1 * | 1/2008 | Mann | 340/573.1 |
| 2008/0092898 A1 | 4/2008 | Schneider et al. | |
| 2009/0064390 A1 * | 3/2009 | Beiring et al. | 2/80 |
| 2009/0128344 A1 * | 5/2009 | Sundaram et al. | 340/573.1 |
| 2009/0212926 A1 | 8/2009 | Du et al. | |
| 2010/0060448 A1 | 3/2010 | Larsen et al. | |
| 2010/0241018 A1 | 9/2010 | Vogel | |
| 2011/0066064 A1 | 3/2011 | Jangle et al. | |

OTHER PUBLICATIONS

A Respiratory Movement Monitoring System Using Fiber-Grating Vision Sensor for Diagnosing Sleep Apnea Syndrome.*
Macmillan Dictionary definition of wear, accessed Jan. 22, 2014, screen captured May 22, 2013.*

* cited by examiner

BABY MONITOR LIGHT

BACKGROUND AND SUMMARY

When some parents bring a newborn baby home, they arrange a bassinet or other baby bed in their bedroom for the infant to sleep in. Parents may do this to make it convenient for the times they need to get up during the night to feed and change their baby. It also gives them comfort, especially new parents, that they can hear if their baby coughs or fusses. There is also an element of uneasiness that is relieved when a parent looks into the bassinet at their sleeping baby, watching the infant's chest rise and lower to the slow cadence of breathing motion. Often times this visual confirmation requires the parent to sit up or get out of bed, turn a light on, lean over and wait for their eyes to adjust and focus. What is needed is a way for a parent or guardian to observe the breathing motion of a sleeping infant from their own bed or another location remote from the infant.

What is disclosed is a baby monitoring light system including a light body having a bottom portion and a top portion, the light body having a height generally shorter than at least one of the light body width and length, the light body comprising a light source oriented upwardly from the top portion, the light body adapted to project a light beam upwardly onto a surface approximately 5 to 15 feet away; and optionally, a blanket comprising a pocket, the light body positionable in the pocket, the pocket having a space through which the light source projects when the light body is in the pocket.

In one alternative, the baby monitoring light system includes a releasable fastener attachable to a blanket.

The baby monitoring light system may include a lantern housing having a desired shape, the lantern housing including an attachment portion having an opening into the lantern housing, the light body releasably attachable to the attachment portion positioned relative to the opening such that the light source is oriented through the opening into the lantern housing.

The baby monitoring system may include a recharging base, and optionally may include a lantern cover over the recharging base.

Also disclosed is a movement monitoring system including a light body having a shape having a bottom portion and a top portion, the light body having a height generally shorter than at least one of the light body width and length, the light body comprising a light source oriented upwardly from the top portion, the light body adapted to project a light beam upwardly onto a surface approximately 5 to 15 feet away; a grid of light detecting sensors positionable on a surface approximately 5 to 15 feet away from the light, the light detecting sensors operatively attached to a controller programmed to receive signals from the light detecting sensors and determine movement of the light across the grid, and an alarm programmed to signal when a determined movement of light across the grid is outside of a predetermined pattern.

A method of monitoring a baby is disclosed including steps of wrapping an infant in a blanket; positioning the infant on its back, attaching a light to the blanket, the light comprising a light body having a shape having a bottom portion and a top portion, the light body having a height generally shorter than at least one of the light body width and length, the light body comprising a light source oriented upwardly from the top portion, the light body adapted to project a light beam upwardly onto a surface approximately 5 to 15 feet away directing the light upwardly to a ceiling or wall. Then, monitoring the movement of the light on the ceiling or wall.

These and other novel features of the subject matter of the present application, as well as details of illustrated embodiments thereof, will be more fully understood from the following description and drawings.

DETAILED DESCRIPTION OF PREFERRED EMBODIMENTS

Figure 1:
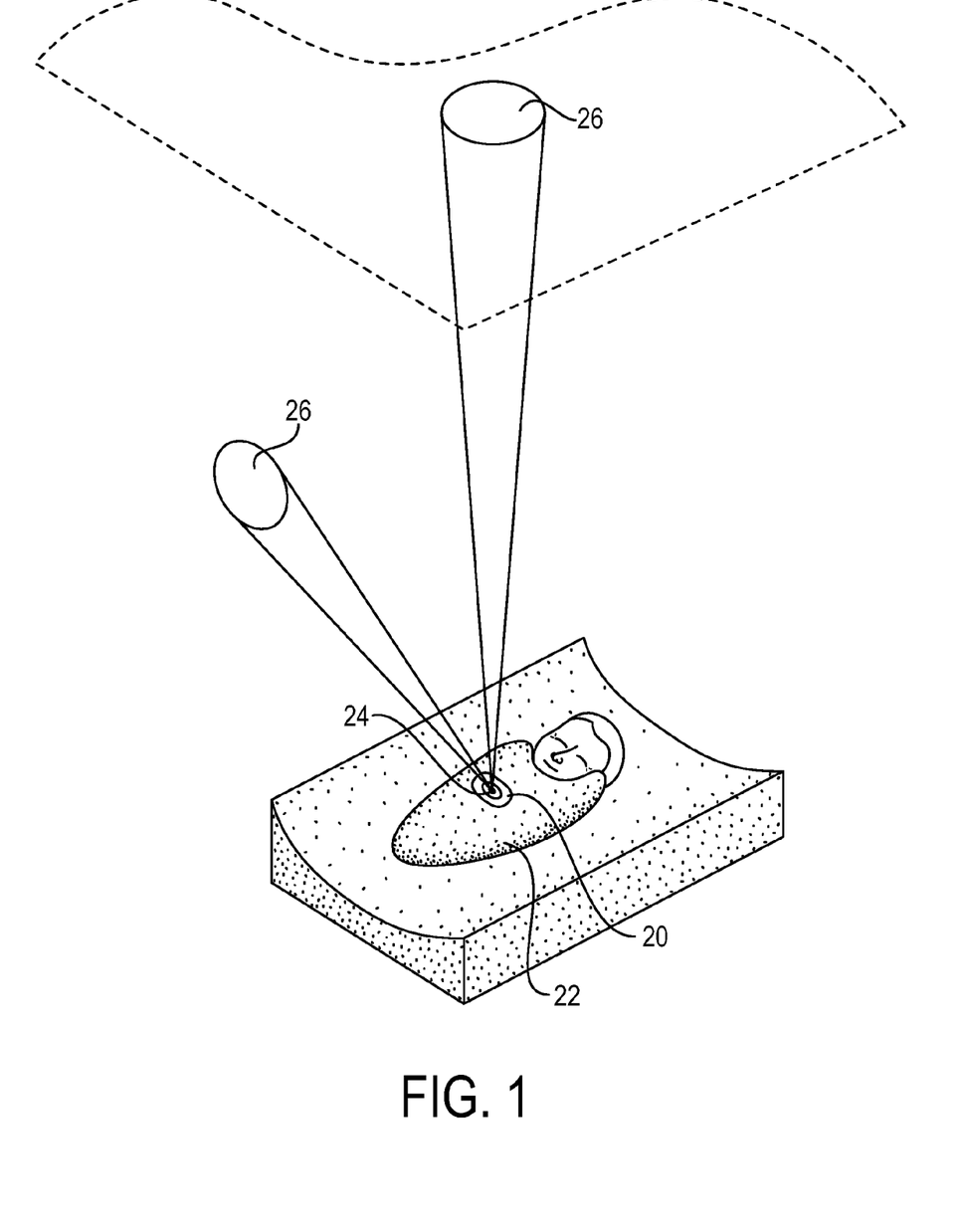
FIG. 1 is a diagrammatical view of the present swaddle light in use positioned on a swaddled infant.

The nature of parents, especially new parents, includes getting up during the night to lean or walk over to the bassinet just to check on their baby. With little or no light in a room it is difficult to focus on the chest movement of the baby, especially when the infant is wrapped in a swaddle blanket. Many parents of newborn babies wrap the infant in a swaddle blanket before placing the baby on her back in a bassinet or crib. The present invention enables the motion of an infant's body to be shown on the ceiling by placing a light source on the swaddled baby's chest or stomach area positioned for the light to shine on the ceiling or an adjacent wall as shown in FIG. 1. Parents can then have that reassuring confirmation by peering into the sleeping baby's room and looking up at the ceiling watching the light beam move back and forth. When the sleeping infant is in the same room as the parent, at night when the parent is in bed, the present invention allows parents of a newborn infant sleeping in a crib or bassinet to have a visual confirmation of their babies breathing movement by simply opening their eyes and looking at a light beam moving on the ceiling.

Figure 2:
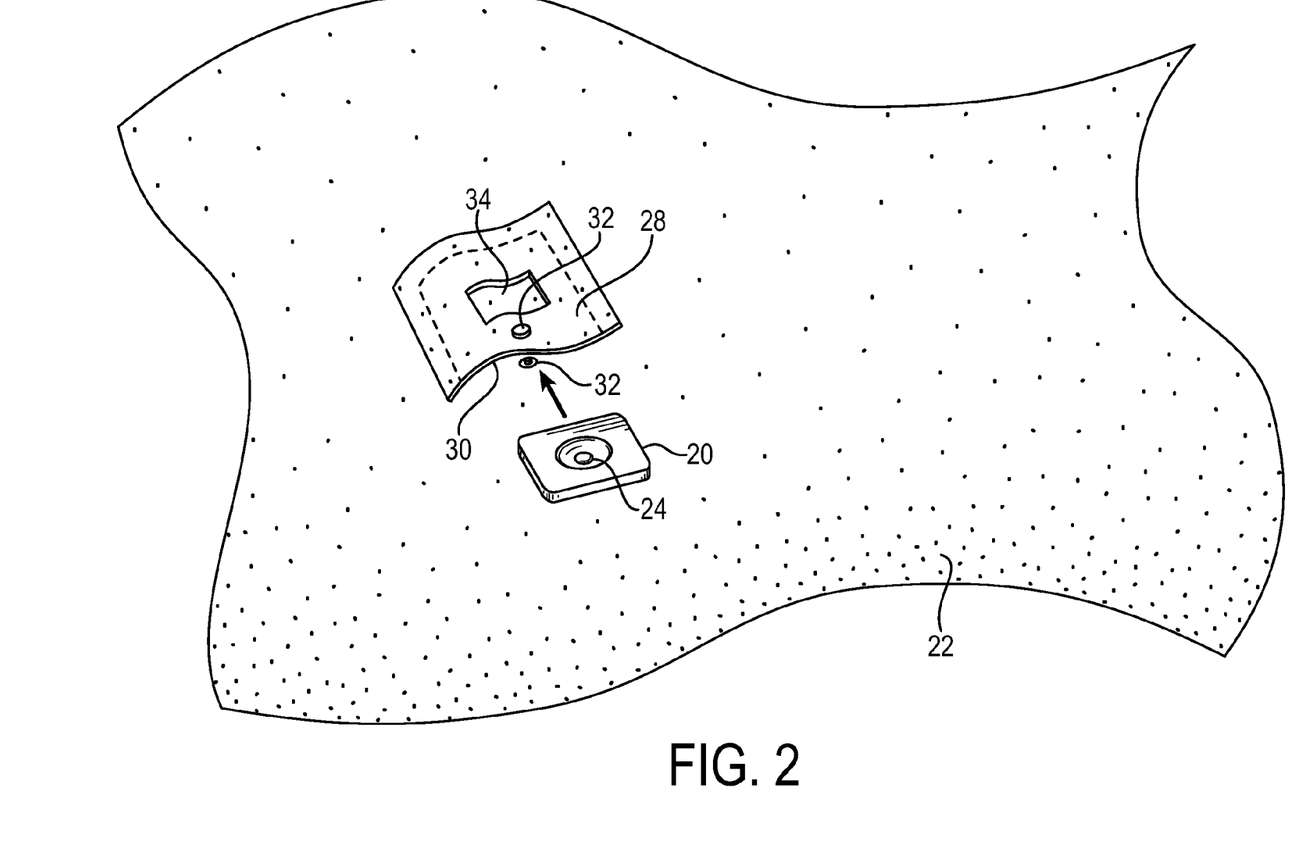
FIG. 2 is a partial diagrammatical view of a swaddle blanket with a pocket for use with a swaddle light of the present disclosure.

Referring now to FIGS. 1 and 2, a swaddle light 20 may be affixed to the outside of a swaddle blanket 22 near the stomach area of a swaddled infant. The swaddle light includes a light source 24 upwardly directed when the swaddle light 20 is positioned on the stomach or chest of a swaddled infant. When positioned as desired, the light beam is directed upwardly to the ceiling or to a nearby wall enabling a spot of light 26 shining on the ceiling or wall to move on the ceiling or wall as the infant's breathing moves the swaddle light 20 up and down. The baby's breathing movement is traced on the ceiling or wall in a projection of light 26.

Figure 3:
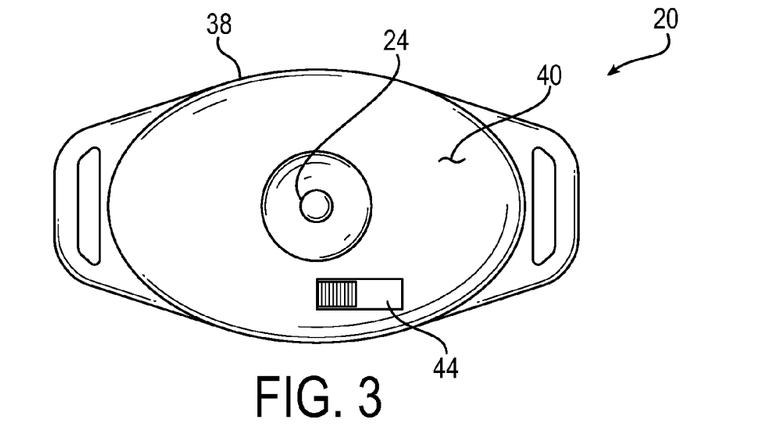
FIG. 3 is a top view of a swaddle light of the present disclosure.

The baby monitoring light system includes means for releasably attaching the swaddle light 20 to a covering such as the swaddle blanket 22, clothing, or other covering of the infant. In one application, the means for releasably attaching the swaddle light 20 may be a pocket 28 on the blanket. The swaddle light 20 may be secured in the pocket 28 on the swaddle blanket 22, the pocket positioned such that the pocket 28 and swaddle light 20 are positioned on the infant's stomach or chest area when the baby is wrapped in the blanket. The swaddle light 20 may be retained in the pocket by closing the pocket opening 30 using one or more fasteners 32 such as snaps, buttons, zippers or other closure. The pocket further includes a space 34 through which the light source 24 can shine outwardly when the swaddle light 20 is positioned in the pocket 28. In particular embodiments, the light space 34 is an aperture or opening in the pocket material. In other embodiments, the light space 34 includes a transparent material that the light shines through. Alternatively or additionally, the means for releasably attaching the swaddle light 20 may be a releaseable fastener 36 such as shown by example in FIGS. 3-4D for removably attaching the swaddle light to a corresponding blanket, or may be attachable to any blanket. The releaseable fastener 36 for attaching the swaddle light may include one or more clips for clipping the light to a blanket, such as alligator clips 36a or pinch clips 36b shown by example in FIGS. 4A and 4B. Alternatively or additionally, the releaseable fastener 36 be a two-part fastener, and the light 20 may include one part of a two-part fastener, with the other part of the two-part fastener affixed to the corresponding blanket, such as snaps 36c or hook and loop material 36d shown by example in FIGS. 4C and 4D. Alternatively, the releasable fastener may be any suitable fastener including buttons and button holes, hook and eye, toggle and loop, toggle and button hole, cord and grommet, strap and buckle, magnet and magnetic, snap clips, buckle clips, zippers, or any other means for removably attaching the swaddle light to a corresponding blanket. In one application, the releaseable fastener 36 for removably attaching the swaddle light to a corresponding blanket includes a grommet or frame sewn onto or attached to the blanket, where the swaddle light removably attaches to the grommet or frame, such as by the swaddle light press-fitting into the grommet or frame, or the swaddle light attaching to the grommet or frame by snap-fit features, or other means for removably attaching the swaddle light to a corresponding blanket. As used in the specification of the application and the appended claims, the term blanket includes woven or non-woven material used as a covering, including bed coverings, swaddling blankets, towels, and apparel.

Figure 7:
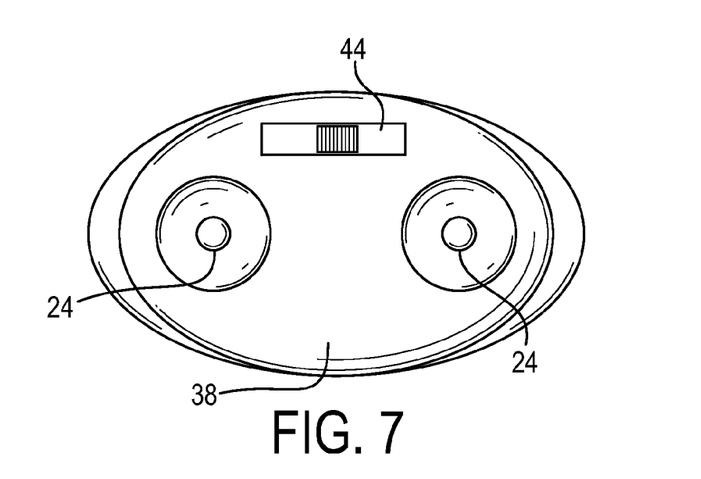
FIG. 7 is a top view of another alternative swaddle light of the present disclosure.

In one alternative, the swaddle light 20 includes a light body 38 such as shown for example in FIGS. 3, 4, 5, and 6. The light body 38 includes an upper surface 40 and a bottom surface 42, the light body 38 having a shape as desired for positioning the light body 38 on the chest or stomach area of a swaddled infant, with the bottom surface 42 facing toward the infant and the upper surface 40 facing away from the infant. As shown in FIGS. 3, 4, 5, and 6, the light body 38 may have a low profile, such as having a height generally shorter than the light body width and length. Alternatively, the light body may have a height generally shorter than one of the length and width. The light body 38 includes the light source 24, positioned in the light body 38 such that a light beam from the light source 24 shines upwardly from the swaddled infant when positioned as desired on the chest or stomach area of a swaddled infant lying on her back. The light source 24 may be oriented in the light body 38 to shine upwardly approximately vertically when a bottom portion is positioned in an approximately horizontal orientation. Alternatively, the light source 24 may be oriented in the light body 38 to shine a light beam upwardly at an angle such that the light shines toward a nearby wall when the light is positioned on the chest or stomach area of a swaddled infant lying on her back. The swaddle light 20 may include two or more light sources 24 shown for example in FIG. 7. In one such alternative, the swaddle light 20 may include at least one light source oriented upwardly to shine a light beam toward the ceiling and at least one light source oriented upwardly at an angle to shine a light beam toward a nearby wall. The light source oriented toward a nearby wall may enable the light beam to be viewed through a video monitor system positioned for a parent or guardian to monitor the baby by video whether or not they are in the same room as the sleeping baby.

The light source 24 includes an on-off switch 44, and a battery (not shown). The battery may be a rechargeable battery, or may be a disposable battery. The light source 24 may be a light emitting diode (LED) bulb. Alternatively, the light source 24 may be a light bulb. In yet another alternative, the light source 24 may be a laser diode. The light source may be provided in any desirable color. The light source may provide a light that is white, red, blue, green, yellow, orange, or any other color suitable for the swaddle light.

In one application, the light may be adjustable in one or more of intensity, focus, and position. For example, the light may include variable power settings to reduce or increase the light intensity as desired. Alternatively or additionally, the light may include a lens movable toward and away from the light source, such as by rotating on a threaded embossment, adjustable to increase and decrease the size of the light beam displayed on the ceiling or wall. In another example, the light source may be mounted in a movable or pivotable carriage such that the angle of the light beam from the light body may be adjusted.

Figure 3A:
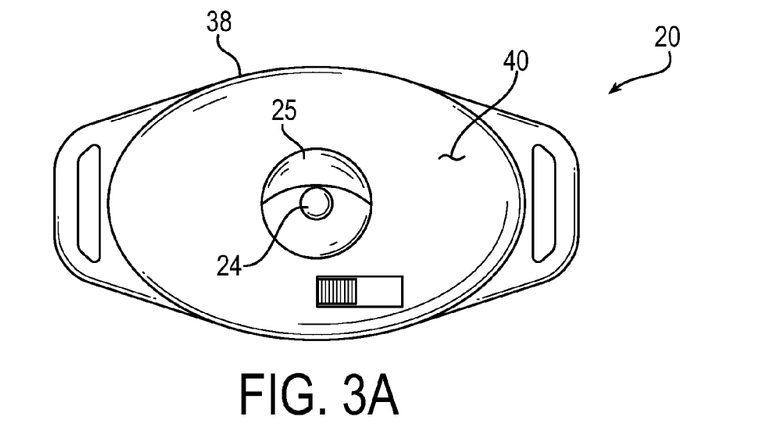
FIG. 3A is a top view of a swaddle light of the present disclosure according to another embodiment.
Figure 3B:
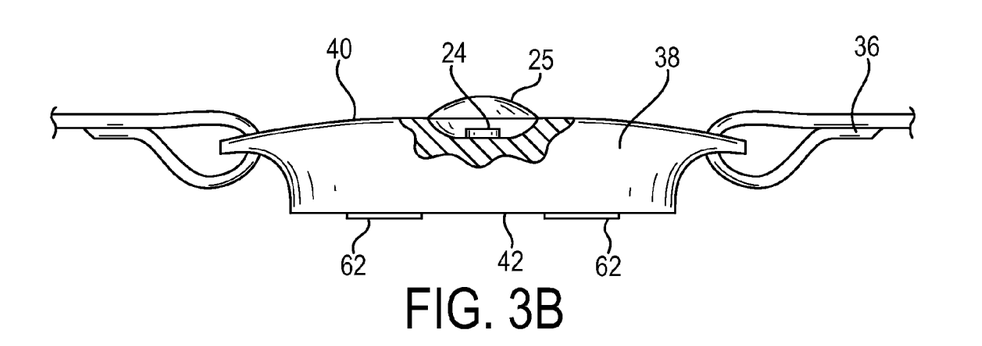
FIG. 3B is a side view with a partial cross section of the swaddle light of FIG. 3A.
Figure 4:
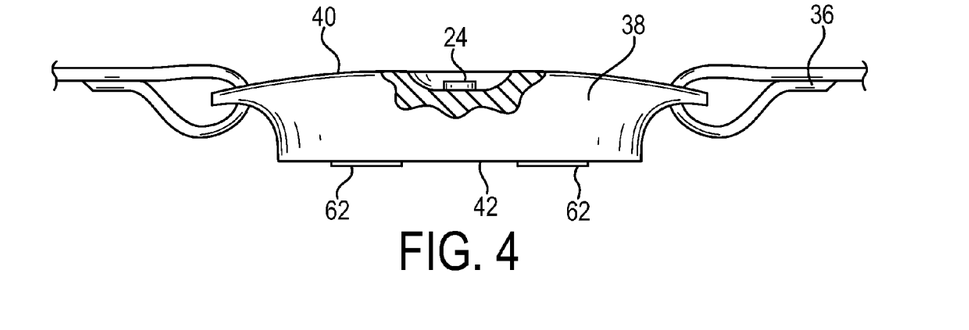
FIG. 4 is a side view with a partial cross section of the swaddle light of FIG. 3.
Figure 4A:
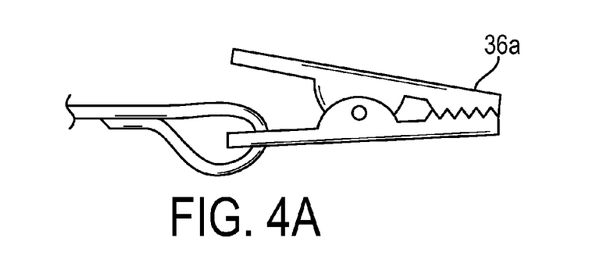
FIGS. 4A-4D are partial diagrammatical detail views of alternative releasable fasteners for use with the swaddle light of FIG. 4.
Figure 4B:
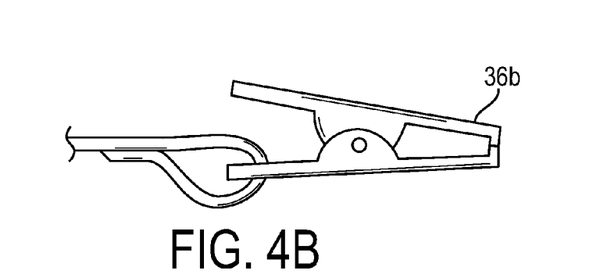
Figure 4C:
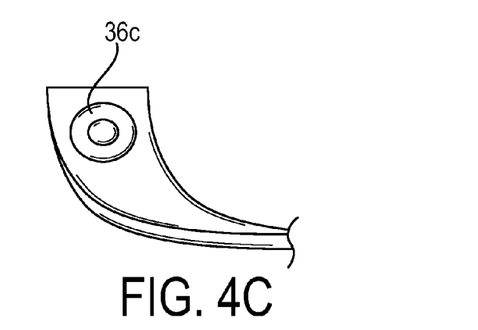
Figure 4D:
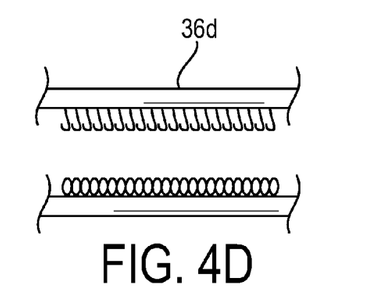
Figure 5:
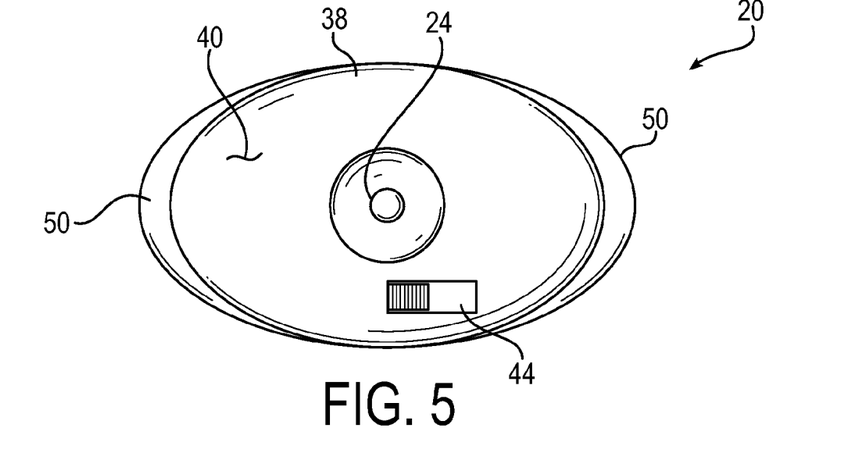
FIG. 5 is a top view of an alternative swaddle light of the present disclosure.
Figure 6:
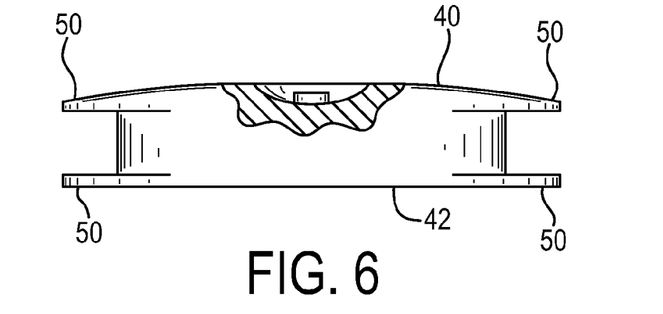
FIG. 6 is a side view with a partial cross section of the alternative swaddle light of FIG. 5.

In certain applications, the light source may be recessed into the light body such that the glow of the light source is not in the infant's line of sight or peripheral vision when in use. Alternatively, a shielding rib, protrusion, or other feature 25 may be positioned around at least a portion of the sides of the light source 24 to shield the glow of the light from the infant as shown in FIGS. 3A and 3B.

In certain applications, particularly with video monitored applications, the light source may be invisible or nearly invisible to the naked eye in the infrared, near-infrared, ultraviolet, or near ultraviolet wavelengths. In this alternative, the invisible or nearly invisible wavelength light may be captured and amplified using 'night vision' technology or any other method or technology to view non-visible light. In certain such applications, the light source may include an infrared light source, near-infrared light source, ultraviolet light source, and/or near-ultraviolet light source.

An alternative method of the present invention includes placing a reflector on the swaddle blanket, and then positioning a light source strategically placed elsewhere in the room, oriented such that the light source is directed to the reflector, whereby at least a portion of the light is reflected by the reflector upwardly to the ceiling or wall. In yet another alternative, the light source may be an invisible or near invisible wavelength as discussed above. This reflected invisible or near invisible light could be captured and amplified using 'night vision' technology or any other method or technology to view non-visible light.

Figure 8:
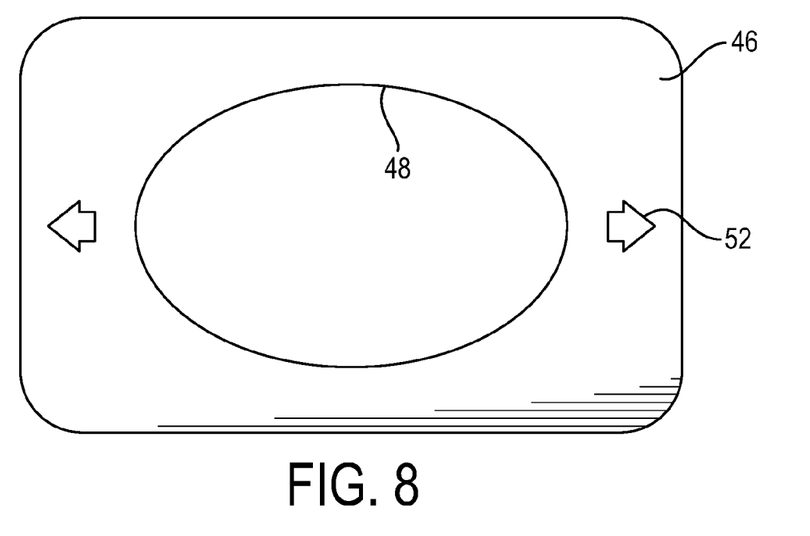
FIG. 8 is a top view of an outer portion for the swaddle light shown in FIG. 5.
Figure 9:
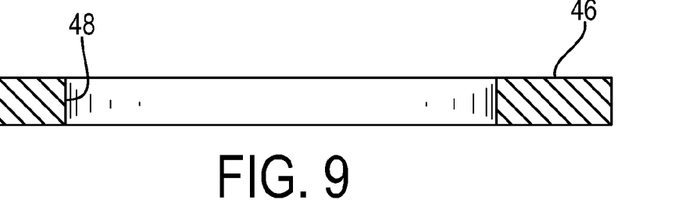
FIG. 9 is a side view of the outer portion shown in FIG. 8.
Figure 10:
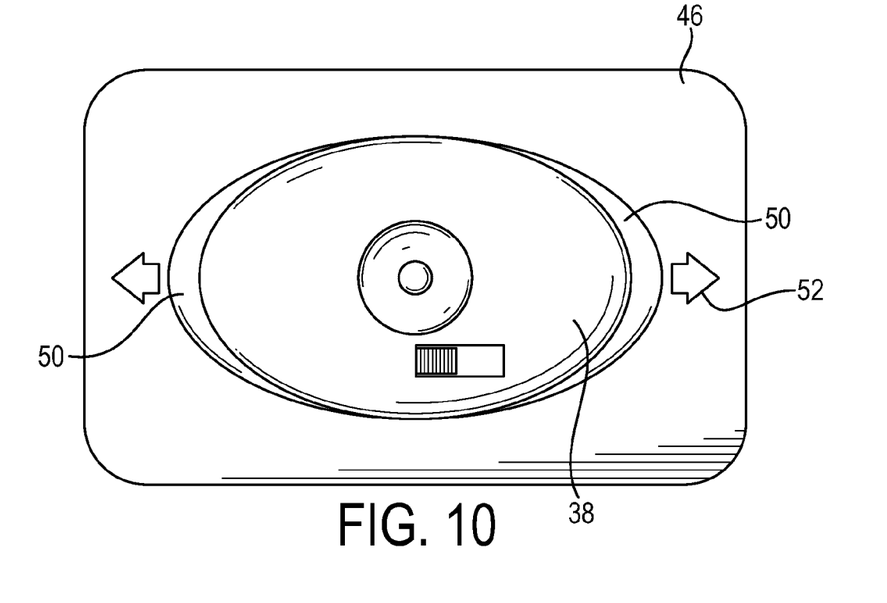
FIG. 10 is a top view of the light of FIG. 5 installed in the outer portion of FIG. 8 forming a swaddle light of the present disclosure.

The swaddle light 20 may include the light body 38 and an outer portion 46 such as shown for example in FIGS. 8 and 9. The outer portion 46 may be a polymeric shape as desired for positioning and handling the swaddle light 20. Alternatively, the light body 38 may be attached into a patch of cloth. The swaddle light 20 could also be integrally part of the swaddle blanket 22 if the light is water resistant for laundering of the blanket. However, the swaddle light 20 being removable from the blanket enables laundering of the blanket without the light being in the blanket. In the alternative shown in FIGS. 8-10, the light body 38 is removable from the outer portion. In the example shown in FIGS. 8 and 9, the outer portion 46 includes an attachment portion 48 forming an aperture, and is made of an elastomeric material with the aperture 48 being stretchable around the light body 38 to install the light body 38 in the outer portion 46 as shown in FIG. 10. In this example, the light body may include one or more tabs 50 extending from the upper surface 40 and bottom surface 42 retaining the light body 38 in the outer portion 46. Graphical indicators such as arrows 52 and/or text may be provided on the outer portion providing instructions as to how to install the light body into the outer portion.

Alternatively, the light body 38 may attach to the outer portion 46 using snap-fit features. Alternatively or additionally, the light body may be threaded into the outer portion, attached by fasteners, integrally formed into the outer portion, or otherwise attached to the outer portion by any desired technique.

The light body 38 and outer portion 46 may be made from a polymeric material. In one application, at least a portion of the light body 38 and/or outer portion 46 is made from a relatively flexible elastomeric material, such as having a durometer between about 40 to 80 on the Shore 00 scale, or alternatively having a durometer between about 20 and 80 on the Shore A scale. In other alternatives, the materials used may be semi-rigid (approximately 30 to 55 Shore D) or rigid (approximately 55 to 95 Shore D) materials as desired for the application. It is contemplated that for certain applications in which an infant or small child may handle the light, the materials used will be appropriately soft.

Figure 11:
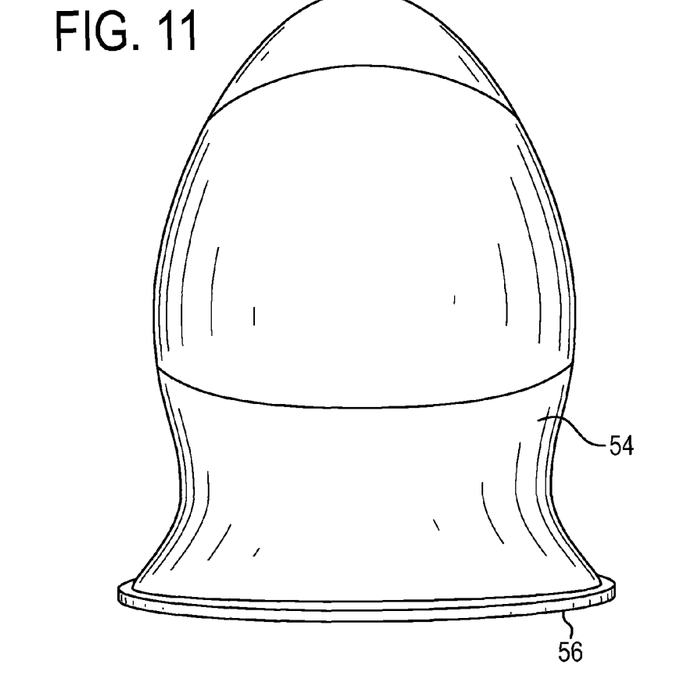
FIG. 11 is a perspective view of a lantern housing of the present disclosure.
Figures 12, 13:
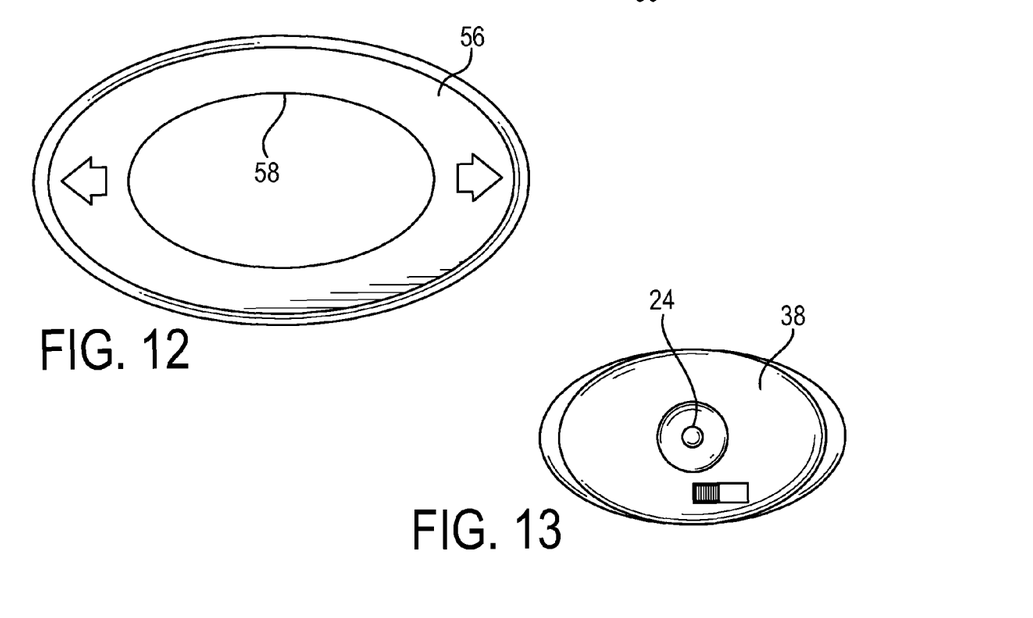
FIG. 12 is a bottom view of the lantern housing of FIG. 11.
FIG. 13 is the light of FIG. 5 for use with the lantern housing shown in FIG. 11.

The swaddle light 20 is useful during the period of time an infant is wrapped in a swaddle blanket at bedtime. After a child is able to roll over, the swaddle light may not remain in an orientation desired by the parent or guardian. However, the light body 38 may be adapted for multiple uses. In one application, the light body may be adapted for use as a flashlight for parents to use when changing diapers or feeding in the night. In another application, the light body 38 may be used in conjunction with a lantern housing 54, shown by example in FIG. 11, such as for a night light, or for a child to play with, or a parent to use for light when changing diapers or feeding in the night. In one example, the lantern housing 54 may be a hollow or partially hollow housing having a base portion 56. In the alternative shown in FIGS. 11 and 12, the light body 38 is attachable to the lantern housing 54. In the example shown in FIGS. 11 and 12, the lantern housing 54 includes an attachment portion 58 forming an opening into the lantern housing, and is made of an elastomeric material with the attachment portion 58 being stretchable around the light body 38 to install the light body 38 in the lantern housing 54. As with the example discussed with respect to FIG. 5, the light body may include one or more tabs 50 extending from the upper surface 40 and bottom surface 42 retaining the light body 38 in the lantern housing 54. As such, a light system may include the swaddle blanket 22, the light 20, and a lantern housing 54, where the light body 38 is attachable to the blanket, or alternatively to the lantern housing 54, as desired.

Alternatively, the light body 38 may attach to the lantern housing 54 using snap-fit features. Alternatively or additionally, the light body may be threaded into the lantern housing, attached by fasteners, integrally formed into the outer portion, or otherwise attached or attachable to the lantern housing by any desired technique.

The lantern housing 54 may be made, at least in part, of a translucent material, and may include a reflector on the inside of the housing 54 to reflect the light from the light source 24 inside the housing to provide a desired light distribution. Alternatively or additionally, a light diffuser may be provided inside the housing 54 to provide a desired light distribution. In one alternative, at least a portion of the lantern housing is molded from a light diffusing material.

The lantern housing 54 may be made from a polymeric material. In one application such as shown by example in FIGS. 11 and 12, at least a portion of the lantern housing 54 is made from a relatively flexible elastomeric material, such as having a durometer between about 40 to 80 on the Shore 00 scale, or alternatively having a durometer between about 20 and 80 on the Shore A scale. In other alternatives, the materials used may be semi-rigid (approximately 30 to 55 Shore D) or rigid (approximately 55 to 95 Shore D) materials as desired for the application. It is contemplated that for certain applications in which an infant or small child may handle the lantern housing, the materials used will be appropriately soft.

Figure 14:
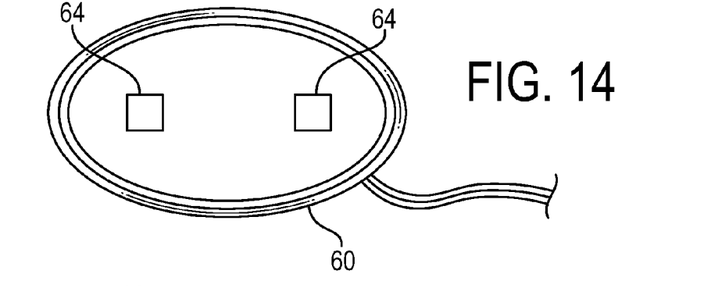
FIG. 14 is a top view of a recharging base of the present disclosure.
Figure 15:
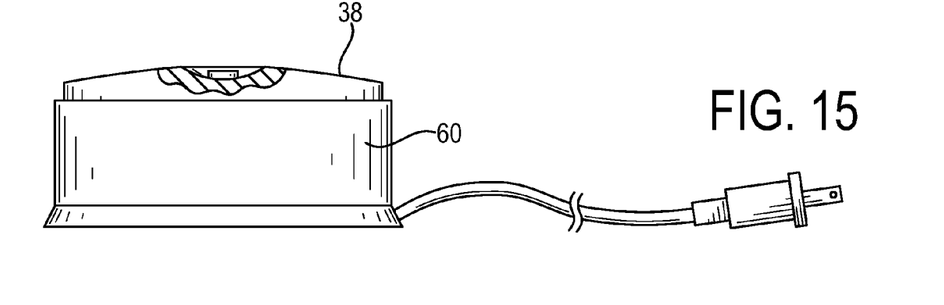
FIG. 15 is a side view with a partial cross section of the recharging base of FIG. 14 with a light positioned on the recharging base.

The light may be powered by a rechargeable battery. In such embodiments, the battery may be recharged by placing or plugged the light body 38 onto a charging system. In one alternative, the charging system may include a recharging base 60 shown for example in FIGS. 14 and 15. In this embodiment, the bottom portion 42 of the light body may include contacts 62 through which electricity can be applied to recharge the battery. Base contacts 64 may be provided in the recharging base 60 positioned corresponding to the light contacts 62 when the light body 38 is positioned on the recharging base 60 such as shown for example in FIG. 15. In another alternative, the rechargeable battery may be recharged using inductive charging, in which the light need only be placed on or near the recharging base. In this alternative, a first inductive coil may be positioned in the recharging base and a second inductive coil positioned in the light body to create an electromagnetic field therebetween as is known in the art.

Figure 16:
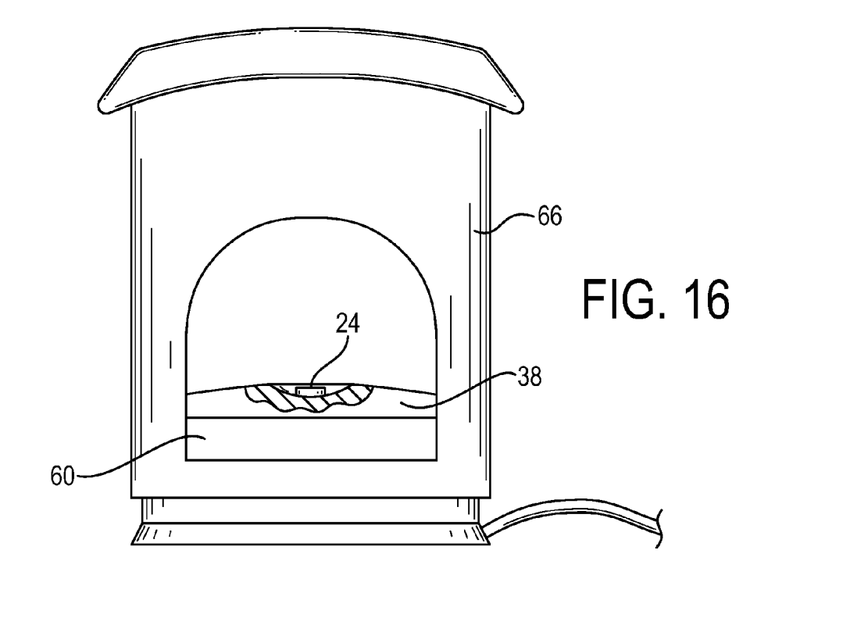
FIG. 16 is a side view with a partial cross section of the recharging base of FIG. 15 with a lantern cover.

The light body 38 may be useful as a light when positioned on the recharging base 60 by providing a lantern cover 66 such as shown for example in FIG. 16. The lantern cover 66 may be a hollow or partially hollow housing removably positionable over the recharging base 60 by lifting the cover 66 off of and onto the base. Alternatively or additionally, the lantern cover 66 may attach to the recharging base 60 using snap-fit features. Alternatively or additionally, the lantern cover may be threaded into the recharging base, attached by fasteners, integrally formed into the base, or otherwise attached or attachable to the recharging base by any desired technique.

The lantern cover 66 may be made, at least in part, of a translucent material, and may include a reflector on the inside of the cover 66 to reflect the light from the light source 24 inside the cover to provide a desired light distribution. Alternatively or additionally, a light diffuser may be provided inside the cover 66 to provide a desired light distribution. In one alternative, at least a portion of the lantern cover is molded from a light diffusing material.

The lantern cover 66 may be made from a polymeric material. In one application such as shown by example in FIG. 16, at least a portion of the lantern cover 66 is made from a relatively flexible elastomeric material, such as having a durometer between about 40 to 80 on the Shore 00 scale, or alternatively having a durometer between about 20 and 80 on the Shore A scale. In other alternatives, the materials used may be semi-rigid (approximately 30 to 55 Shore D) or rigid (approximately 55 to 95 Shore D) materials as desired for the application. It is contemplated that for certain applications in which an infant or small child may handle or contact the lantern cover, the materials used will be appropriately soft.

Figure 17:
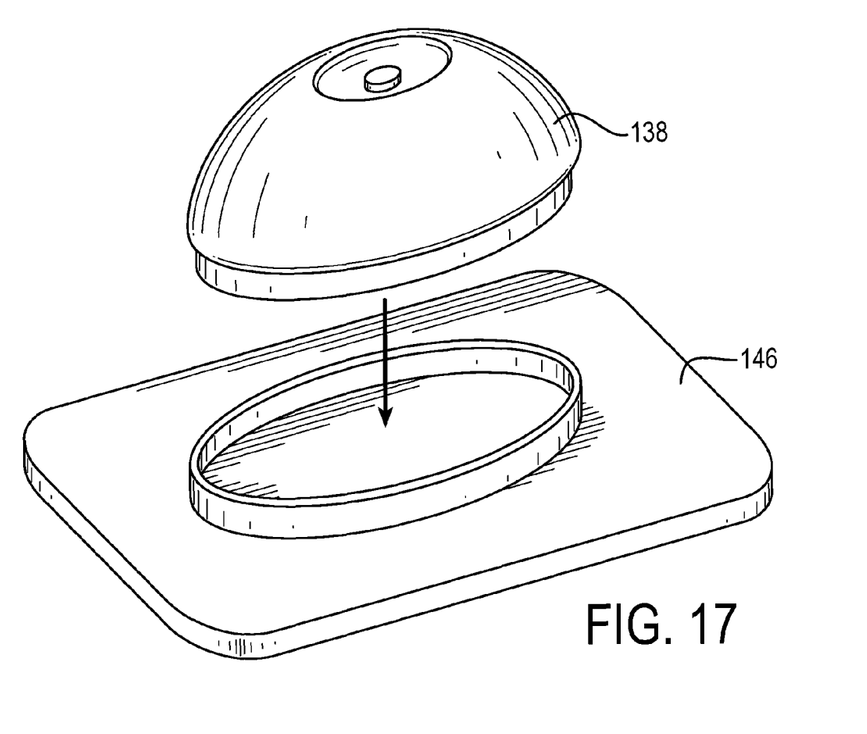
FIG. 17 is yet another alternative swaddle light of the present disclosure.
Figure 18:
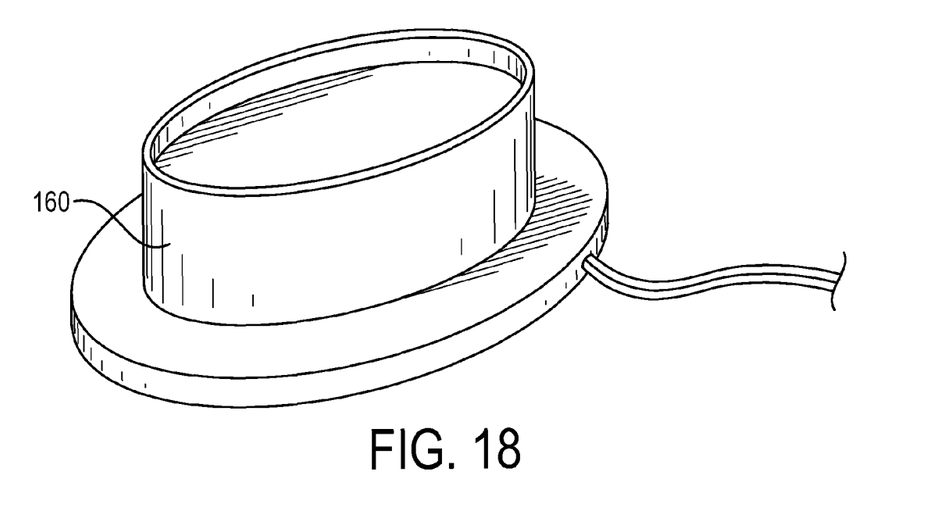
FIG. 18 is an alternative recharging base for use with the alternative light of FIG. 17.

It is contemplated that the shape of the light body may be any shape as desired for the application and as desirable by the consumer. In one alternative shown for example in FIG. 17, the light body 138 may have a rounded or arcuate shape and fit with corresponding outer portion 146. A recharging base 160 may be provided in any shape corresponding to the shape of the light body 138.

The present swaddle light may be provided as a baby monitoring light system, in which the light body 38 may be provided with the swaddle blanket 22 and/or one or more accessories, such as the recharging base 60, the lantern housing 54, the lantern cover 66, or other accessories for utilizing the light. It is contemplated that the swaddle light and accessories may be provided in various colors, shapes, and fashions suitable for the tastes and needs of the users.

A method of monitoring an infant may include steps of wrapping an infant in a blanket; positioning the infant on its back, attaching a light to the blanket, the light comprising a light body having a shape having a bottom portion and a top portion, the light body having a height generally shorter than the light body width and length, the light body comprising a light source oriented upwardly from the top portion, the light body adapted to project a light beam upwardly onto a surface approximately 5 to 15 feet away directing the light upwardly to a ceiling or wall. Then, monitoring the movement of the light on the ceiling or wall.

In particular embodiments, the present swaddle light is a passive visual monitor for a parent's or guardian's quick confirmation of a baby's breathing motion without specialized monitoring machines by projecting a beam of light corresponding to that movement onto a ceiling or wall. Alternatively or additionally, when the light is directed to a nearby wall, the light may be visible within the area of a video camera for a video monitor. In this way, a viewer may see the described movement on the screen of a video monitor system, which is typically too small to directly view breathing movement of an infant.

Figure 19:
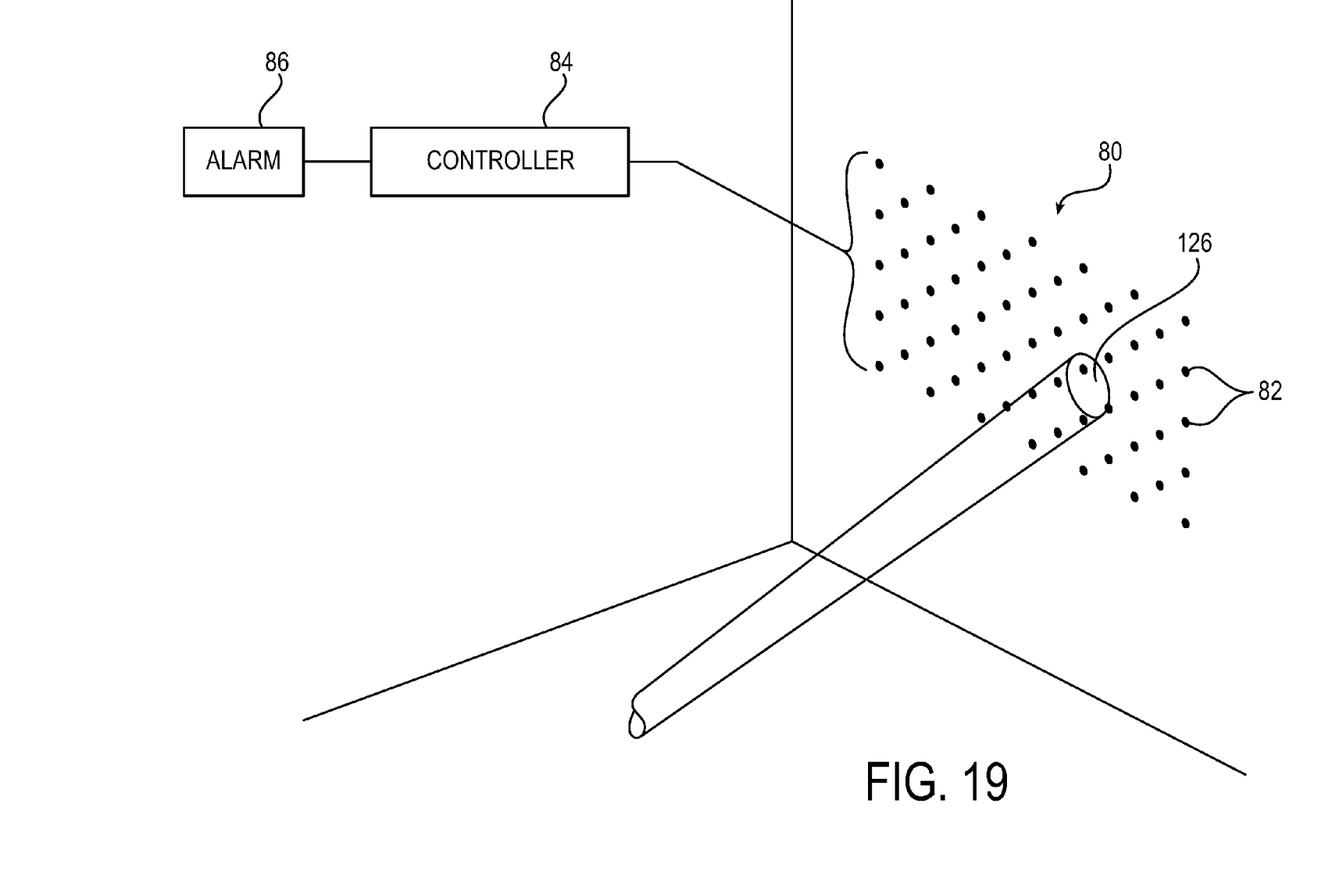
FIG. 19 is a diagrammatical view of a projection of a light on a sensor grid.

While certain embodiments are not intended to be an active alert in case of emergency situations, it is contemplated that for certain applications, the present light could be used for automated monitoring of an infant's movement, or for other applications under which a small movement of a person, an animal, or an object is desired to be monitored automatically. In an automated application, a sensor grid 80 such as shown in FIG. 19 may be provided having a grid of a plurality of photocells 82 or other light detecting sensors connected to a controller 84 such as a programmable logic controller or a computer programmed to receive signals from the light sensors and determine movement of the projection of light 126 across the grid. The light may be attached to the monitored subject using a means for attachment such as discussed above with the particular embodiments, or other fastening techniques useful for the particular application, and then the light projected onto the grid, the controller monitoring the sensors indicating movement of light across the grid. In particular embodiments, a predetermined pattern of movement or movement within a grid sensor area is established across the grid as the monitored subject moves. The controller may activate an alarm 86 or another action or output as desired when a determined movement of light across the grid is outside of the predetermined pattern or grid area. For example, when the light motion is first exposed to the grid, the pattern of movement or movement within a grid sensor area is established and saved into memory as a desired pattern. Then if the pattern of light movement changes from the stored movement pattern or grid area in an amount outside of an expected range of variation, the alarm or other action could be signaled. For other applications for objects where movement is not desired, the light would normally be stationary on the sensor grid, and unexpected movement sensed by the sensors could trigger an alarm or other output. Various automated applications may include monitoring in dependent care, health care, or similar environments, process monitoring, security monitoring, or other applications.

In the automated applications, the grid of photocells or light detecting sensors could be installed on site, or may be installed in a portable screen or film that is attached or erected in a desired location. For particular applications, the portable screen can be set up and later taken down for use with temporary installations. The grid may follow a square, rectangular, or other pattern, and include a sufficient number of photocells or sensors to provide the accuracy needed for the application.

In particular embodiments, a movement monitoring system comprises a light body having a shape having a bottom portion and a top portion, where the light body may have a height generally shorter than at least one of the light body width and length, the light body including a light source oriented outwardly from the top portion, the light body adapted to project a light beam outwardly onto a surface approximately 5 to 15 feet away. The system includes a grid of light detecting sensors positionable on said surface approximately 5 to 15 feet away from the light source, the light detecting sensors operatively attached to a controller programmed to receive signals from the light detecting sensors and determine movement of the light beam across the grid, and an alarm programmed to signal when a determined movement of light across the grid is outside of a predetermined pattern.

A method of automatically monitoring movement of a subject, such as a person, animal, or object, may include steps of attaching a light to the monitored subject, the light including a light body having a shape with a bottom portion and a top portion, where the light body may have a height generally shorter than the light body width and length, the light body comprising a light source oriented upwardly from the top portion, the light body adapted to project a light beam upwardly onto a surface approximately 5 to 15 feet away directing the light upwardly to a ceiling or wall. The method includes providing a grid of light detecting sensors positionable on said surface approximately 5 to 15 feet away from the light source, the light detecting sensors operatively attached to a controller programmed to receive signals from the light detecting sensors and determine movement of the light beam across the grid, and programming an alarm to signal when a determined movement of light across the grid is outside of a predetermined pattern. Then, monitoring the sensors and activating the alarm if the controller determines that movement of light across the grid is outside of the predetermined pattern.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected by the appended claims and the equivalents thereof.

What is claimed is:

1. A baby monitoring light system comprising
a passive visual monitor for confirmation of a baby's breathing motion, the passive visual monitor including:
a blanket including an inside surface facing toward the baby and an outer surface facing away from the baby;
a means for releasably attaching a light to the blanket in a location configured to be arranged on or near the baby's chest or stomach area; and
the light releasably attached to the blanket, the light comprising:
a light body having a bottom portion and a top portion, the light body having a height generally shorter than at least one of the light body width and length,
the light body including a light source oriented outwardly from the top portion,
the light body adapted to project a light beam outwardly from the outer surface of the blanket and onto a surface approximately 5 to 15 feet away for directing the light outwardly to a ceiling or wall and monitoring movement of the light beam on the ceiling or wall due to the baby's breathing motion.

2. The baby monitoring light system of claim 1, the means for releasably attaching being a pocket, the system further comprising:
the blanket having the pocket, the light positionable in the pocket, the pocket having a space through which the light source projects when the light body is in the pocket.

3. The baby monitoring light system of claim 2, where the space in the pocket is an opening in the blanket material.

4. The baby monitoring light system of claim 2, where the space in the pocket includes a transparent material.

5. The baby monitoring light system of claim 1, the light body further comprising a rechargeable battery, the bottom portion comprising contacts through which electricity can be applied to recharge the battery.

6. The baby monitoring light system of claim 1, the light source oriented upwardly approximately vertically when the bottom portion is positioned in an approximately horizontal orientation.

7. The baby monitoring light system of claim 1, the light source oriented upwardly at an angle from vertical when the bottom portion is positioned in an approximately horizontal orientation.

8. The baby monitoring light system of claim 1, where the light source is one selected from the group consisting of a reflector, a light emitting diode, a light bulb, an infrared light source, and a laser diode.

9. The baby monitoring light system of claim 1, where the light source is adjustable in one or more of intensity, focus, and position.

10. The baby monitoring light system of claim 1, further comprising
a grid of light detecting sensors positionable on said surface approximately 5 to 15 feet away from the light source, the light detecting sensors operatively attached to a controller programmed to receive signals from the light detecting sensors and determine movement of the light beam across the grid, and
an alarm programmed to signal when a determined movement of light across the grid is outside of a predetermined pattern.

11. A method of monitoring a baby comprising:
passive visual monitoring for confirmation of a baby's breathing motion, the passive visual monitoring including:
wrapping a baby in a blanket, the blanket including an inside surface facing toward the baby and an outer surface facing away from the baby;
positioning the baby on its back;
attaching a light to the blanket, in a location configured to be arranged on or near the baby's chest or stomach area, the light comprising:
a light body having a bottom portion and a top portion;
the light body including a light source oriented outwardly from the top portion;
the light body adapted to project a light beam outwardly from the outer surface of the blanket and onto a surface approximately 5 to 15 feet away, directing the light outwardly to a ceiling or wall; and
monitoring movement of the light beam on the ceiling or wall due to the baby's breathing motion.

12. The method of monitoring a baby of claim 11, where the step of attaching a light to a blanket comprises positioning the light in a pocket on the blanket, the pocket having a space through which the light source projects when the light body is in the pocket.

13. The method of monitoring a baby of claim 11, where the light source is one selected from the group consisting of a reflector, a light emitting diode, a light bulb, an infrared light source, and a laser diode.

14. The method of monitoring a baby of claim 1, further comprising
adjusting the light in one or more of intensity, focus, and position.

15. The baby monitoring light system of claim 1, further comprising a shielding rib or protrusion positioned around at least a portion of the light source for shielding the glow of the light source from the baby's line of sight or peripheral vision when in use.

16. The baby monitoring light system of claim 1, where the light source is recessed into the light body such that the glow of the light source is shielded from the baby's line of sight or peripheral vision when in use.

* * * * *